(12) United States Patent
Shiraishi (10) Patent No.: US 9,261,463 B2
(45) Date of Patent: Feb. 16, 2016

(54) VISUAL INSPECTION APPARATUS

(71) Applicant: UENO SEIKI CO., LTD., Onga-Gun, Fukuoka (JP)

(72) Inventor: Kazunari Shiraishi, Onga-gun (JP)

(73) Assignee: UENO SEIKI CO., LTD., Fukuoka (JP)

( * ) Notice: Subject to any disclaimer, the term of this patent is extended or adjusted under 35 U.S.C. 154(b) by 0 days.

(21) Appl. No.: 14/453,321

(22) Filed: Aug. 6, 2014

(65) Prior Publication Data

US 2015/0062329 A1    Mar. 5, 2015

(30) Foreign Application Priority Data

Sep. 2, 2013 (JP) ................................. 2013-181288

(51) Int. Cl.
*G01N 21/88* (2006.01)
*G01N 21/956* (2006.01)

(52) U.S. Cl.
CPC ...... *G01N 21/8806* (2013.01); *G01N 21/95684* (2013.01); *G01N 2021/8841* (2013.01)

(58) Field of Classification Search
CPC ................. G01N 2021/8841; G01N 21/8806; G01N 21/95684; H05K 13/08
See application file for complete search history.

(56) References Cited

FOREIGN PATENT DOCUMENTS

| JP | 64-35205 A | 2/1989 |
|---|---|---|
| JP | 11-326235 A | 11/1999 |
| JP | 2000-230813 | * 8/2000 |
| JP | 2000-230813 A | 8/2000 |
| JP | 2000-337843 A | 12/2000 |
| JP | 2003-254726 A | 9/2003 |
| JP | 2008-241342 | * 9/2008 |
| JP | 2008-241342 A | 10/2008 |

OTHER PUBLICATIONS

Notification of Reasons for Refusal issued by JPO on Japanese Patent Application No. 2013-181288, dated Dec. 3, 2013, with English translation. (5 pages).

* cited by examiner

*Primary Examiner* — Dave Czekaj
*Assistant Examiner* — Md Haque
(74) *Attorney, Agent, or Firm* — Westerman, Hattori, Daniels & Adrian, LLP (57) ABSTRACT

A visual inspection apparatus 10 performing a visual inspection of an electronic component 13 including opposing sides 11, 11a and opposing sides 12, 12a, the apparatus 10 including an optical-path adjusting means 30 changing a traveling direction of a light and setting an appearance of the side 11a of the electronic component 13 temporarily stopped at a first inspection point in an image of the side 11 of the electronic component 13 captured by a first imaging means 31, and an optical-path adjusting means 34 setting an appearance of the side 12a of the electronic component 13 temporarily stopped at a second inspection point in an image of the side 12 of the electronic component 13 captured by a second imaging means 35, thereby performing a visual inspection of the sides 11, 11a, 12, 12a.

7 Claims, 4 Drawing Sheets

VISUAL INSPECTION APPARATUS

TECHNICAL FIELD

The present invention relates to a visual inspection apparatus operable to inspect an appearance of an electronic component by imaging the electronic component.

BACKGROUND ART

Various electronic components, including bare chips and CSPs (Chip Sized Packages), are shipped after a predetermined inspection. A visual inspection apparatus is used for detecting any crack or chip of the electronic component. Specific examples of the apparatus are described, for example, in Patent Literatures 1 and 2. A visual inspection apparatus disclosed in Patent Literature 1 detects if problems in appearance are present or an absent by imaging an appearance of an electronic component (a semiconductor device) with a camera, in which the electronic component being rectangular or square when viewed from above is placed in a recess of an embossed tape. In the vicinity of the embossed tape, a plurality of reflecting mirrors are provided so that a total of three surfaces, a pair of opposing sides and a surface (top side), of the electronic component can be imaged by the one camera. A visual inspection apparatus disclosed in Patent Literature 2 performs an a visual inspection by imaging a pair of opposing sides and a surface (top side) of an electronic component with a camera while feeding the electronic component by a conveyer-belt mechanism.

CITATION LIST

Patent Literature

Patent Literature 1: Japanese Unexamined Patent Application Publication No. 2003-254726
Patent Literature 2: Japanese Unexamined Patent Application Publication No. 2000-337843

SUMMARY OF INVENTION

Technical Problem

The visual inspection apparatuses disclosed in Patent Literatures 1 and 2 with restrictions of layouts of the reflecting mirrors and the camera cannot image the rest pair of opposing sides. Thus, the visual inspection of all the four sides cannot be performed.

The present invention has been made in view of the above circumstances and it is an object of the present invention to provide a visual inspection apparatus operable to inspect appearances of all four sides of an electric component.

Solution to Problem

To accomplish the above object, the present invention provides a visual inspection apparatus performing an a visual inspection of an electronic component including opposing sides A, B and opposing sides C, D, the electronic component being rectangular or square when viewed from above, the apparatus comprising: a rotating body including a plurality of supporting members circularly attached to the rotating body with gaps between the supporting members, the supporting members each holding the electronic component, the rotating body intermittently rotating to temporarily stop the electronic component at one and the other of the first and second inspection points in series, the electronic component held by the supporting member in a way that the sides A, B are along a rotating direction and one of the sides C, D is placed on an upstream side from the other of the sides C, D in the rotating direction; a first imaging means imaging the side A of the electronic component temporarily stopped at the first inspection point; an optical-path adjusting means b changing a traveling direction of a light and setting an appearance of the side B of the electronic component temporarily stopped at the first inspection point in an image of the side A of the electronic component, the image about to be captured by the first imaging means; a second imaging means imaging the side C of the electronic component temporarily stopped at the second inspection point; and an optical-path adjusting means d changing a traveling direction of a light and setting an appearance of the side D of the electronic component temporarily stopped at the second inspection point in an image of the side C of the electronic component, the image about to be captured by the second imaging means; wherein drive sources each provided in the first and second inspection points to move the supporting members back and forth independently are provided, and the visual inspection of the sides A, B, C, D of the electronic component is performed; and the sides A, B of the electronic component held by the supporting member are imaged after the supporting member set to a back position is fed to the first inspection point and is moved forward, and the sides C, D of the same are imaged after the supporting member set to the back position is fed to the second inspection point and is moved forward.

In the visual inspection apparatus according to the present invention, it is preferable to further provide an optical-path adjusting means a equalizing lengths of an optical path from the side A of the electronic component temporarily stopped at the first inspection point to the first imaging means and an optical path from the side B of the electronic component temporarily stopped at the first inspection point to the first imaging means; and an optical-path adjusting means c equalizing lengths of an optical path from the side C of the electronic component temporarily stopped at the second inspection point to the second imaging means and an optical path from the side D of the electronic component temporarily stopped at the second inspection point to the second imaging means.

In the visual inspection apparatus according to the present invention, it is preferable that the optical-path adjusting means a, b, c, d each comprise a prism.

In the visual inspection apparatus according to the present invention, it is preferable that the sides A, B, C, D of the electronic component are each laterally long, the first imaging means obtains an image of the parallely-arranged sides A, B of the electronic component, and the second imaging means obtains an image of the parallely-arranged sides C, D of the electronic component.

In the visual inspection apparatus according to the present invention, it is preferable to provide a component supply means detaching the electronic component from a wafer with the plural electronic components aligned and supplying the electronic component to the supporting member.

Advantageous Effects of Invention

Since the visual inspection apparatus according to the present invention includes (a) the optical-path adjusting means b changing the traveling direction of the light and setting the appearance of the side B of the electronic component temporarily stopped at the first inspection point in the image of the side A of the electronic component about to be captured by the first imaging means and (b) the optical-path adjusting means d changing the traveling direction of the light and setting the appearance of the side D of the electronic component temporarily stopped at the second inspection point in the image of the side C of the electronic component about to be captured by the second imaging means, the apparatus can perform the visual inspection of the sides A, B, C, and D of the electronic component.

DESCRIPTION OF EMBODIMENTS

Figure 1:
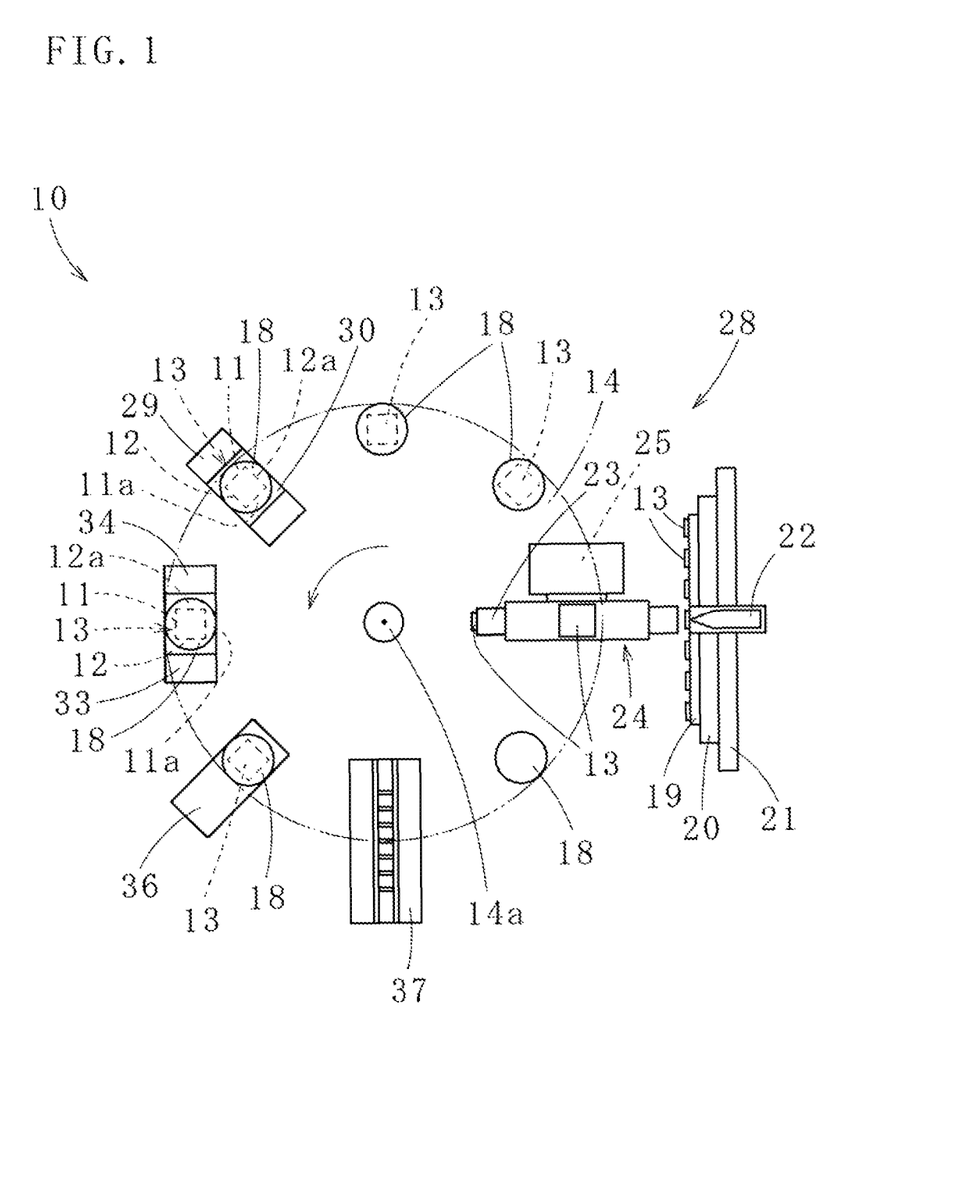
FIG. 1 is a plan view of an visual inspection apparatus according to an embodiment of the present invention.

Referring to the accompanying drawings, embodiments of the present invention will be described for a better understanding of the present invention. As shown in FIG. 1, a visual inspection apparatus 10 according to an embodiment of the present invention is an apparatus to inspect an appearance of an electronic component 13 being rectangular or square when viewed from above. The electronic component 13 includes opposing sides 11, 11a (sides A, B) and opposing sides 12, 12a (sides C, D). Hereinafter, a detail description will be given on the visual inspection apparatus 10.

Figure 2:
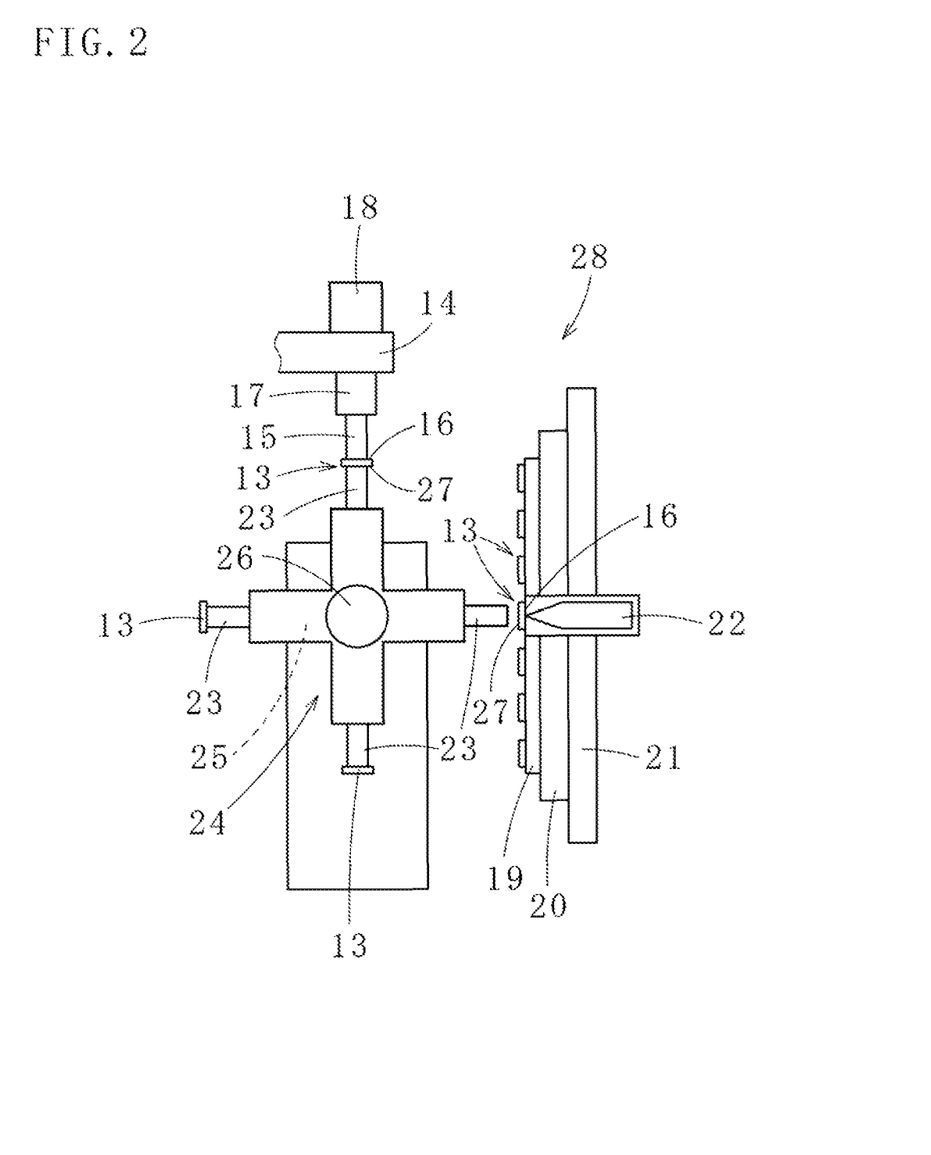
FIG. 2 is an explanatory diagram showing a component supply means handing an electronic component to a supporting member.

As shown in FIGS. 1 and 2, the visual inspection apparatus 10 includes a circular plate 14, an example of rotating bodies, and a plurality of supporting members 15 attached to the circular plate 14.

The horizontally-arranged circular plate 14 is given a drive force (driven) by an unillustrated servomotor via a rotating shaft 14a coupled to a center of the circular plate 14 to rotate around the rotating shaft 14a in one direction. The rotating shaft 14a is arranged vertically.

The plural supporting members 15 are attached to the circular plate 14 such that the supporting members 15 are arranged circularly along a circumferential direction of the circular plate 14 with predetermined gaps between the supporting members 15. The servomotor intermittently rotates the circular plate 14 predetermined degrees (45° in this embodiment) to move the plural supporting members 15 simultaneously. In a single operation of the servomotor, each of the supporting members 15 moves a distance equivalent to a pitch (an interval) between the supporting members 15 in a rotating direction of the circular plate 14 and stops temporarily.

As shown in FIG. 2, each of the supporting members 15 is attached to the circular plate 14 while being held by a guide mechanism 17 such that the supporting member 15 can move up and down. At each point where the supporting member 15 stops temporarily, as shown in FIGS. 1 and 2, a servomotor 18, an example of drive sources, is fixed above the supporting member 15 by an unillustrated supporting section. Each of the servomotors 18 gives a drive force to the supporting member 15 located below the servomotor 18 and moves the supporting member 15 up and down (an example of back-and-forth motions) independently. The supporting member 15 can be moved back and forth, for example, in a direction inclined to a vertical direction instead of being moved up and down.

In this embodiment, a vertically-long nozzle is used to hold the electronic component 13 by attaching a top side 16 of the electronic component 13 by a vacuum pressure and to release the held electronic component 13 by a vacuum break.

In the vicinity of the circular plate 14, a wafer 19 with the plural electronic components 13 aligned thereon is fixed by a wafer ring (wafer ring frame) 20. The wafer 19 moves with the wafer ring 20 by an operation of a supporting mechanism 21 holding the wafer ring 20.

At a rear side of the vertically-arranged wafer 19, a pin 22 is positioned, which is movable in a horizontal direction. The supporting mechanism 21 adjusts a position of the wafer 19 with the wafer ring 20 to set an electronic component 13 to be detached from the wafer 19 in front of the pin 22. Hereinafter, the electronic component 13 set in front of the pin 22 is also referred to as the detachable-target electronic component 13.

In the vicinity of the wafer 19 fixed to the wafer ring 20, a rotary mechanism 24 including a plurality of nozzles 23 is provided. The rotary mechanism 24 is fixed to a horizontal shaft 26 coupled to a servomotor 25 and is given a drive force by the servomotor 25 via the horizontal shaft 26. Thereby, the rotary mechanism 24 rotates predetermined degrees intermittently and sequentially sets each of the nozzles 23 to face to the detachable-target electronic component 13. The nozzles 23 can each hold the electronic component 13 by attaching a bottom side 27 of the electronic component 13 by a vacuum pressure and can release the held electronic component 13 by a vacuum break.

The pin 22 moves toward the wafer 19 and touches to the wafer 19 so as to push the detachable-target electronic component 13 toward the nozzle 23 facing to the detachable-target electronic component 13.

The bottom side 27 of the electronic component 13 pushed by the pin 22 is touched and attached to the nozzle 23, thereby the electronic component 13 is detached from the wafer 19.

The nozzle 23 holding the electronic component 13 is moved by a rotation of the rotary mechanism 24 to set the held electronic component 13 at a point where the electronic component 13 is delivered to the supporting member 15 (hereinafter, also referred to as a "transferring point").

Above the electronic component 13 set at the transferring point, the temporarily-halted supporting member 15 is located. The supporting member 15 is pulled down by the operation of the servomotor 18 (this servomotor 18 is not illustrated in FIG. 1). As shown in FIG. 2, the supporting member 15 touches to the top side 16 of the electronic component 13 held by the nozzle 23 and attaches the top side 16 of the electronic component 13 by the vacuum pressure.

When the supporting member 15 attaches the electronic component 13, the nozzle 23 loses hold of the electronic component 13 by the vacuum break. After the nozzle 23 releases the electronic component 13, the supporting member 15 is elevated by the operation of the servomotor 18 and is then moved by the rotation of predetermined degrees of the circular plate 14. The circular plate 14 rotates the predetermined degrees in a state where all the supporting members 15 are arranged in elevated points (an example of back positions).

In this embodiment, a component supply means 28 to pick up the electronic component 13 from the wafer 19 and to supply the electronic component 13 to the supporting member 15 is made up mainly of the wafer ring 20, the supporting mechanism 21, the pin 22, the rotary mechanism 24, the servomotor 25, and the horizontal shaft 26.

As shown in FIG. 1, the supporting member 15 holds the electronic component 13 such that the horizontally-long sides 11 and 11a are along the rotating direction of the circular plate 14 and one of the horizontally-long sides 12 and 12a is located on an upstream side from the other of the sides 12 and 12a in the rotating direction of the circular plate 14. In this embodiment, the sides 11 and 11a are respectively located on a radially outward side and a radially inward side of a theoretical circle with the plural supporting members 15 arranged thereon, and the sides 12 and 12a are respectively located on a downstream side and the upstream side in the rotating direction of the circular plate 14. However, the sides 11 and 11a can be positioned oppositely. The sides 12 and 12a can be positioned oppositely, too.

At the point where the supporting member 15 temporarily stops, (a) a first inspection point to perform the visual inspection of the sides 11 and 11a of the electronic component 13 and (b) a second inspection point to perform the visual inspection of the sides 12 and 12a of the electronic component 13 are provided apart from the transferring point. The first inspection point is located on the upstream side from the second inspection point in the rotating direction of the circular plate 14. By rotating predetermined degrees for multiple times, the circular plate 14 makes the electronic component 13 held by the supporting member 15 at the transferring point temporarily halted at the first inspection point. Furthermore, by rotating the predetermined degrees for one time, the circular plate 14 moves the electronic component 13 temporarily halted at the first inspection point to the second inspection point. In short, the circular plate 14 intermittently rotates and temporarily stops the electronic component 13 held by the supporting member 15 at the first and second inspection points in series.

Here, the first inspection point can be located at the downstream side from the second inspection point in the rotating direction of the circular plate 14. When the first inspection point is located at the downstream side from the second inspection point in the rotating direction of the circular plate 14, the electronic component 13 held by the supporting member 15 temporarily stops at the second inspection point and thereafter temporarily stops at the first inspection point.

Thus, the electronic component 13 temporarily stops at one and the other of the first and second inspection points in series, which means that (a) an electronic component 13 temporarily stops at the first inspection point and thereafter temporarily stops the at the second inspection point and (b) an electronic component 13 temporarily stops at the second inspection point and thereafter temporarily stops at the first inspection point.

Figure 3:
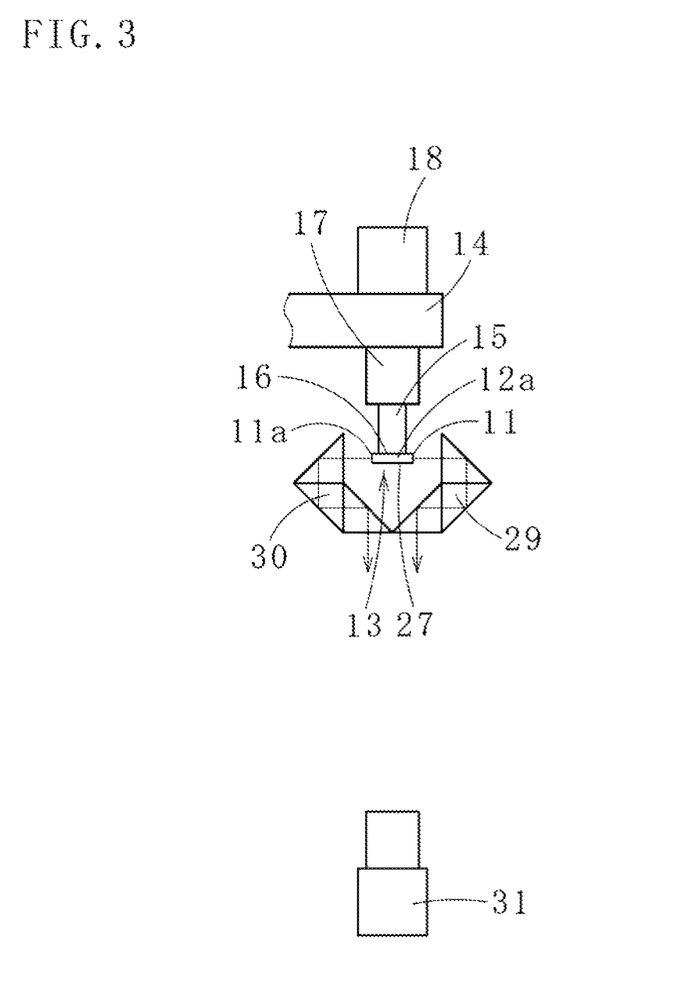
FIG. 3 is an explanatory diagram showing an electronic component being imaged at a first inspection point.

As shown in FIGS. 1 and 3, prisms 29 and 30 are provided at the first inspection point, and a camera 31 (an example of first imaging means) is provided below the prisms 29 and 30.

The supporting member 15 holding the electronic component 13 while being set at the elevated point is fed to and temporarily halted at the first inspection point, and thereafter is descended (moved forward) to a descended point (an example of forward positions) by the operation of the servomotor 18 provided at the first inspection point. The prisms 29 and 30 each includes a part located at the level of the electronic component 13 held by the supporting member 15 descended at the first inspection point. The part is arranged in one side and the other side (i.e., the sides 11 and 11a) of the electronic component 13 in a radial direction of the circular plate 14 with a predetermined gap between the part and the sides.

The camera 31 is fixed such that an imaging direction thereof faces upward to the electronic component 13 located at the first inspection point. The prism 29 reflects a light (i.e., changes a traveling direction of a light) multiple times (three times in this embodiment), allowing the side 11 of the electronic component 13 temporarily halted at the first inspection point to fit in an image captured by the camera 31. Then, the camera 31 images the side 11 of the electronic component 13 temporarily halted at the first inspection point.

Like the prism 29, the prism 30 reflects a light (i.e., changes a traveling direction of a light) multiple times (three times in this embodiment), allowing the side 11a of the electronic component 13 temporarily halted at the first inspection point to fit in an image captured by the camera 31. Accordingly, the prism 30 changes the traveling direction of the light and sets the appearance of the side 11a of the electronic component 13 temporarily halted at the first inspection point in the image of the side 11 of the electronic component 13 being imaged by the camera 31. In short, the sides 11 and 11a can be imaged by one camera 31.

In this embodiment, a light-path adjusting means "a" to change the traveling direction of the light is provided, including the prism 29 and an unillustrated holding mechanism to fix the prism 29. Likewise, a light-path adjusting means "b" to change the traveling direction of the light is provided, including the prism 30 and an unillustrated holding mechanism to fix the prism 30.

In addition, the prism 29 makes (a) an optical path from the side 11 of the electronic component 13 temporarily halted at the first inspection point to the camera 31 and (b) an optical path from the side 11a of the electronic component 13 temporarily halted at the first inspection point to the camera 31 via the prism 30 the same length (the substantially same length). As the optical paths from the sides 11 and 11a of the electronic component 13 temporarily halted at the first inspection point to the camera 31 are the same length, the camera 31 can set each appearance of the sides 11 and 11a in one image while focusing on both the sides 11 and 11a.

The camera 31 is connected to an unillustrated calculator. The calculator detects whether the sides 11 and 11a have cracks or chips based on the image of the sides 11 and 11a of the electronic component 13 taken by the camera 31. When the camera 31 obtains an image in which the sides 11 and 11a of the electronic component 13 are arranged in parallel to each other, the camera 31 can capture the wider appearances of the sides 11 and 11a in a range where the camera 31 can image than when the camera 31 captures an image in which the sides 11 and 11a are in an another arrangement (e.g., the sides 11 and 11a are arranged in series). As a result, the calculator can perform the high-accuracy visual inspection of the sides 11 and 11a.

Depending on a degree of accuracy required for the visual inspection of the sides 11 and 11a of the electronic component 13, it is not necessary to equalize the lengths of the optical paths from the sides 11 and 11a of the electronic component 13 temporarily halted at the first inspection point to the camera 31, and it is not necessary for the camera 31 to obtain the image in which the sides 11 and 11a of the electronic component 13 are arranged in parallel to each other.

For example, instead of providing the light-path adjusting means a, the following configuration is possible: the camera 31 is arranged at the same level as the electronic component 13 with the imaging direction thereof facing to the side 11 so that the camera 31 can be oriented to a direction in which the camera 31 can directly image the side 11, and the light-path adjusting means b sets the appearance of the side 11a in the image of the side 11 being taken by the camera 31.

Furthermore, the camera 31 does not have to capture the parallely-arranged sides 11 and 11a in the image.

Figure 4:
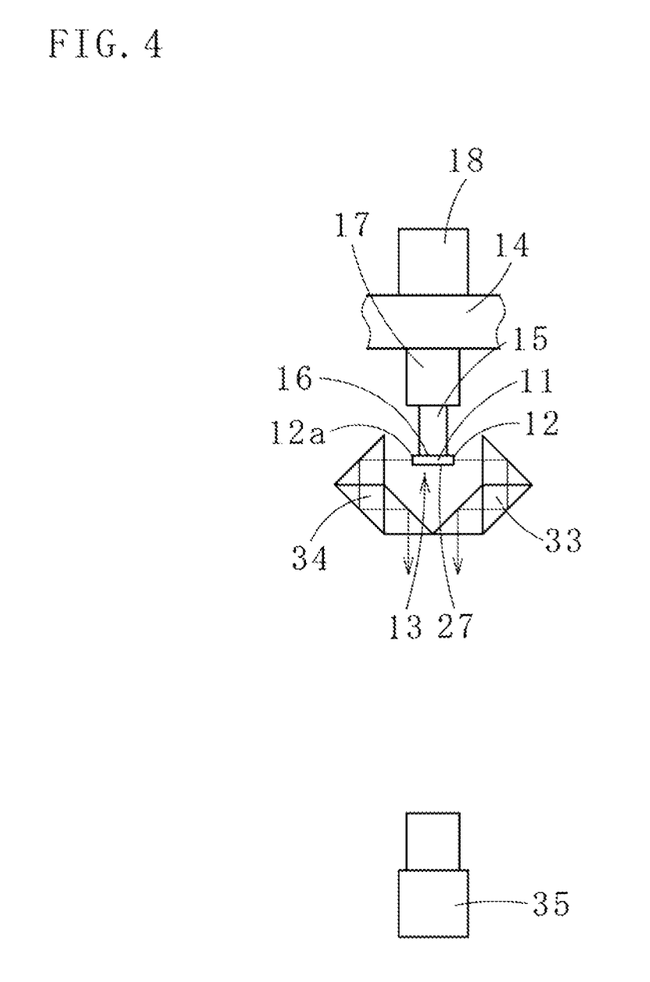
FIG. 4 is an explanatory diagram showing an electronic component being imaged at a second inspection point.

As shown in FIGS. 1 and 4, prisms 33 and 34 are provided at the second inspection point, and a camera 35 (an example of second imaging means) is provided below the prisms 33 and 34.

The supporting member 15 holding the electronic component 13 while being set at the elevated point is fed to and temporarily halted at the second inspection point, and thereafter is descended (moved forward) to a descended point (forward position) by the operation of the servomotor 18 provided at the second inspection point. In FIGS. 2 to 4, a description of a mechanism that transmits the drive force of the servomotor 18 to the supporting member 15 is omitted.

The prisms 33 and 34 each includes a part located at the level of the electronic component 13 held by the supporting member 15 descended at the second inspection point. The part is arranged with predetermined gaps between the part and the downstream and upstream sides (i.e., the sides 12 and 12a) of the electronic component 13 in the radial direction of the circular plate 14.

The camera 35 is fixed such that an imaging direction thereof faces upward to the electronic component 13 located at the second inspection point. The prism 33 reflects a light (i.e., changes a traveling direction of a light) multiple times (three times in this embodiment), allowing the side 12 of the electronic component 13 temporarily halted at the second inspection point to fit in an image captured by the camera 35. Then, the camera 35 images the side 12 of the electronic component 13 temporarily halted at the second inspection point.

Like the prism 33, the prism 34 reflects a light (i.e., changes a traveling direction of a light) multiple times (three times in this embodiment), allowing the side 12a of the electronic component 13 temporarily halted at the second inspection point to fit in an image captured by the camera 35. Accordingly, the prism 34 changes the traveling direction of the light and sets the appearance of the side 12a of the electronic component 13 temporarily halted at the second inspection point in the image of the side 12 of the electronic component 13 being imaged by the camera 35. In short, the sides 12 and 12a can be imaged by one camera 35.

In this embodiment, a light-path adjusting means "c" to change the traveling direction of the light is provided, including the prism 33 and an unillustrated holding mechanism to fix the prism 33. Likewise, a light-path adjusting means "d" to change the traveling direction of the light is provided, including the prism 34 and an unillustrated holding mechanism to fix the prism 34.

In addition, the prism 33 makes (a) an optical path from the side 12 of the electronic component 13 temporarily halted at the second inspection point to the camera 35 and (b) an optical path from the side 12a of the electronic component 13 temporarily halted at the second inspection point to the camera 35 via the prism 34 the same length (the substantially same length). As the optical paths from the sides 12 and 12a of the electronic component 13 temporarily halted at the second inspection point to the camera 35 are the same length, the camera 35 can set each appearance of the sides 12 and 12a in one image while focusing on both the sides 12 and 12a.

The camera 35 is also connected to the calculator that is connected to the camera 31. The calculator detects whether the sides 12 and 12a have cracks or chips based on the image of the sides 12 and 12a of the electronic component 13 taken by the camera 35. In this embodiment, the calculator obtains ignorable patterns of appearances in advance based on images each capturing the sides 11, 11a, 12, and 12a of the non-defective electronic component 13 without cracks or chips to detect a present or an absent of a defect in appearance. Using the ignorable patterns of the appearances, the calculator detects whether the sides 11, 11a, 12, and 12a have cracks or chips.

When the camera 35 obtains an image in which the sides 12 and 12a of the electronic component 13 are arranged in parallel to each other, the camera 35 can capture the wider appearances of the sides 12 and 12a in a range where the camera 35 can image than when the camera 35 captures an image in which the sides 12 and 12a are in an another arrangement. As a result, the calculator can perform the high-accuracy visual inspection of the sides 12 and 12a.

Depending on a degree of accuracy required for the visual inspection of the sides 12 and 12a of the electronic component 13, it is not necessary to equalize the lengths of the optical paths from the sides 12 and 12a of the electronic component 13 temporarily halted at the second inspection point to the camera 35, and it is not necessary for the camera 35 to obtain the image in which the sides 12 and 12a of the electronic component 13 are arranged in parallel to each other.

In the downstream side from the second inspection point in the rotating direction of the circular plate 14, as shown in FIG. 1, a sorter 36 is provided to eject the electronic component 13 with the cracks or chips detected as a defective product. In the downstream side from the sorter 36 in the rotating direction of the circular plate 14, a taping unit 37 is provided to put the electronic component 13 in a taping (tape). In FIG. 1, a description of the servomotor 18 placed above the taping unit 37 is omitted. Obviously, it is possible to provide a unit to perform a visual inspection of the top side 16 and the bottom side 27 of the electronic component 13 and a unit to correct the position of the electronic component 13 in the upstream side from the first inspection point in the rotating direction of the circular plate 14.

Hereinabove, the embodiments of the present invention are described. The present invention is not limited to the above-described embodiments, but can include any modifications within a scope of the present invention.

For example, the rotating body does not have to be the circular plate, but can be a plate having a shape other than a circle. The rotating body does not even have to be a plate. The rotating shaft of the rotating body does not have to be vertical. For example, the rotating shaft can be horizontal or slanted.

The supporting member does not have to be the nozzle holding the electronic component by the vacuum pressure. For example, the supporting member can hold the electronic component by pinching (clipping) the electronic component. The component supply means can be a mechanism to supply the electronic component from a tray or the taping to the supporting member, or can be a part feeder. Each of the optical-path adjusting means a, b, c, and d can include the prism and the reflecting mirror, or can include the reflecting mirror without the prism.

REFERENCE SIGNS LIST

10: visual inspection apparatus; 11, 11a, 12, 12a: side; 13: electronic component; 14: circular plate; 14a: rotating shaft; 15: supporting member; 16: top side; 17: guide mechanism; 18: servomotor; 19: wafer; 20: wafer ring; 21: supporting mechanism; 22: pin; 23: nozzle; 24: rotary mechanism; 25: servomotor; 26: horizontal shaft; 27: bottom side; 28: component supply means; 29, 30: prism; 31: camera; 33, 34: prism; 35: camera; 36: sorter; 37: taping unit

The invention claimed is:
1. A visual inspection apparatus performing a visual inspection of an electronic component including opposing sides A, B and opposing sides C, D, the electronic component being rectangular or square when viewed from above, the apparatus comprising:

a rotating body configured to rotate in a circular direction, said rotating body comprising a plurality of supporting members circularly attached to the rotating body with gaps between the supporting members, the supporting members each holding the electronic component, the rotating body intermittently rotating to temporarily stop the electronic component at one and the other of the first and second inspection points in series, the electronic component held by the supporting member in a way that the sides A, B are along a rotating direction and one of the sides C, D is placed on an upstream side from the other of the sides C, D in the rotating direction;

a first imaging means imaging the side A of the electronic component temporarily stopped at the first inspection point;

an optical-path adjusting means b changing a traveling direction of a light and setting an appearance of the side B of the electronic component temporarily stopped at the first inspection point in an image of the side A of the electronic component, the image about to be captured by the first imaging means;

a second imaging means imaging the side C of the electronic component temporarily stopped at the second inspection point; and an optical-path adjusting means d changing a traveling direction of a light and setting an appearance of the side D of the electronic component temporarily stopped at the second inspection point in an image of the side C of the electronic component, the image about to be captured by the second imaging means; wherein drive sources each provided in the first and second inspection points to move the supporting members back and forth independently are provided, and the visual inspection of the sides A, B, C, D of the electronic component is performed; and the sides A, B of the electronic component held by the supporting member are imaged after the supporting member set to a back position is fed to the first inspection point and is moved forward, and the sides C, D of the same are imaged after the supporting member set to the back position is fed to the second inspection point and is moved forward.

2. The visual inspection apparatus according to claim 1, further comprising:

an optical-path adjusting means a equalizing lengths of an optical path from the side A of the electronic component temporarily stopped at the first inspection point to the first imaging means and an optical path from the side B of the electronic component temporarily stopped at the first inspection point to the first imaging means; and an optical-path adjusting means c equalizing lengths of an optical path from the side C of the electronic component temporarily stopped at the second inspection point to the second imaging means and an optical path from the side D of the electronic component temporarily stopped at the second inspection point to the second imaging means.

3. The visual inspection apparatus according to claim 2, wherein the optical-path adjusting means a, b, c, d each comprise a prism.

4. The visual inspection apparatus according to claim 2, wherein the plural drive sources each move the supporting member back and forth to move the supporting member up and down, the optical-path adjusting means a, b each include a part located at a height of the electronic component held by the supporting member descended at the first inspection point, and the optical-path adjusting means c, d each include a part located at a height of the electronic component held by the supporting member descended at the second inspection point.

5. The visual inspection apparatus according to claim 1, wherein the sides A, B, C, D of the electronic component are each laterally long, the first imaging means obtains an image of the parallely-arranged sides A, B of the electronic component, and the second imaging means obtains an image of the parallely-arranged sides C, D of the electronic component.

6. The visual inspection apparatus according to claim 1, comprising:

a component supply means detaching the electronic component from a wafer with the plural electronic components aligned and supplying the electronic component to the supporting member.

7. A visual inspection apparatus performing a visual inspection of an electronic component including opposing sides A, B and opposing sides C, D, the electronic component being rectangular or square when viewed from above, the apparatus comprising:

a rotating body including a plurality of supporting members circularly attached to the rotating body with gaps between the supporting members, the supporting members each holding the electronic component, the rotating body intermittently rotating to temporarily stop the electronic component at one and the other of the first and second inspection points in series, the electronic component held by the supporting member in a way that the sides A, B are along a rotating direction and one of the sides C, D is placed on an upstream side from the other of the sides C, D in the rotating direction;

a first imaging means imaging the side A of the electronic component temporarily stopped at the first inspection point;

an optical-path adjusting means b changing a traveling direction of a light and setting an appearance of the side B of the electronic component temporarily stopped at the first inspection point in an image of the side A of the electronic component, the image about to be captured by the first imaging means;

a second imaging means imaging the side C of the electronic component temporarily stopped at the second inspection point;

an optical-path adjusting means d changing a traveling direction of a light and setting an appearance of the side D of the electronic component temporarily stopped at the second inspection point in an image of the side C of the electronic component, the image about to be captured by the second imaging means;

an optical-path adjusting means a equalizing lengths of an optical path from the side A of the electronic component temporarily stopped at the first inspection point to the first imaging means and an optical path from the side B of the electronic component temporarily stopped at the first inspection point to the first imaging means; and an optical-path adjusting means c equalizing lengths of an optical path from the side C of the electronic component temporarily stopped at the second inspection point to the second imaging means and an optical path from the side D of the electronic component temporarily stopped at the second inspection point to the second imaging means, wherein drive sources each provided in the first and second inspection points to move the supporting members back and forth independently are provided, and the visual inspection of the sides A, B, C, D of the electronic component is performed, the sides A, B of the electronic component held by the supporting member are imaged after the supporting member set to a back position is fed to the first inspection point and is moved forward, and the sides C, D of the same are imaged after the supporting member set to the back position is fed to the second inspection point and is moved forward, the plural drive sources each move the supporting member back and forth to move the supporting member up and down, the optical-path adjusting means a, b each include a part located at a height of the electronic component held by the supporting member descended at the first inspection point, and the optical-path adjusting means c, d each include a part located at a height of the electronic component held by the supporting member descended at the second inspection point.

* * * * *